United States Patent
Brugger et al.

(10) Patent No.: US 7,588,684 B2
(45) Date of Patent: Sep. 15, 2009

(54) SYSTEMS AND METHODS FOR HANDLING AIR AND/OR FLUSHING FLUIDS IN A FLUID CIRCUIT

(75) Inventors: James M. Brugger, Newburyport, MA (US); Dennis M. Treu, Bedford, NH (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 11/742,715

(22) Filed: May 1, 2007

(65) Prior Publication Data
US 2007/0260168 A1 Nov. 8, 2007

Related U.S. Application Data

(60) Continuation of application No. 10/772,888, filed on Feb. 4, 2004, now Pat. No. 7,226,538, which is a division of application No. 09/905,171, filed on Jul. 13, 2001, now abandoned.

(51) Int. Cl.
B01D 61/00 (2006.01)
B01D 36/00 (2006.01)
B01D 61/30 (2006.01)
A61M 37/00 (2006.01)
A61M 39/00 (2006.01)
A61M 39/10 (2006.01)

(52) U.S. Cl. .............. 210/252; 210/194; 210/232; 210/257.1; 210/435; 210/436; 210/472; 604/4.01; 604/6.09; 604/403; 604/411; 604/412

(58) Field of Classification Search ............ 210/194, 210/195.1, 232, 252, 257.1, 258, 436, 435, 210/472, 254; 604/4.01, 5.01, 6.01, 6.09, 604/7, 9
See application file for complete search history.

(56) References Cited

U.S. PATENT DOCUMENTS

| | | | |
|---|---|---|---|
| 2,409,343 A | 10/1946 | Curtis | |
| 3,484,849 A | 12/1969 | Huebner et al. | |
| 3,788,524 A | 1/1974 | Davis et al. | |
| 4,133,314 A | 1/1979 | Bloom et al. | |
| 4,134,402 A | 1/1979 | Mahurkar | |
| 4,144,884 A * | 3/1979 | Tersteegen et al. | 604/74 |
| 4,202,332 A * | 5/1980 | Tersteegen et al. | 604/164.02 |
| 4,439,179 A * | 3/1984 | Lueders et al. | 604/34 |
| 4,585,435 A * | 4/1986 | Vaillancourt | 604/518 |
| 4,787,898 A | 11/1988 | Raines | |
| 4,863,437 A * | 9/1989 | Clarke | 604/246 |

(Continued)

FOREIGN PATENT DOCUMENTS

WO 2001/07136 A1 2/2001

*Primary Examiner*—John Kim
(74) *Attorney, Agent, or Firm*—Miles & Stockbridge P.C.; Mark A. Catan

(57) ABSTRACT

Systems and methods handle air and rinsing fluid during fluid processing. The systems and methods eliminate air from a fluid processing system prior to, during, and after use. The systems and methods provide a connector assembly for establishing fluid flow from a fluid source. The connector assembly has discrete first and second passages that prevent communication between the fluid in first passage and the fluid in the second passage. Prior to system use, the connector assembly may be utilized in a priming function to remove residual air from a fluid circuit prior to use. The connector assembly may also be utilized after use to perform a rinse-back function.

19 Claims, 10 Drawing Sheets

U.S. PATENT DOCUMENTS

| | | |
|---|---|---|
| 4,873,991 A | 10/1989 | Skinner |
| 4,889,529 A | 12/1989 | Haindl |
| 4,980,054 A * | 12/1990 | Lavender ................... 210/90 |
| 5,024,657 A * | 6/1991 | Needham et al. ............. 604/85 |
| 5,211,849 A * | 5/1993 | Kitaevich et al. .......... 604/5.04 |
| 5,368,555 A * | 11/1994 | Sussman et al. ........... 604/6.05 |
| 5,445,630 A | 8/1995 | Richmond |
| 5,484,397 A | 1/1996 | Twardowski |
| 5,533,647 A | 7/1996 | Long-Hsiung |
| 5,698,090 A | 12/1997 | Bene et al. |
| 5,702,597 A | 12/1997 | Chevallet et al. |
| 5,725,776 A | 3/1998 | Kenley et al. |
| 5,744,027 A | 4/1998 | Connell et al. |
| 5,762,805 A | 6/1998 | Truitt et al. |
| 5,772,624 A * | 6/1998 | Utterberg et al. ........... 604/4.01 |
| 5,776,345 A | 7/1998 | Truitt et al. |
| 5,808,181 A | 9/1998 | Wamsiedler et al. |
| 5,846,419 A | 12/1998 | Nederlof |
| 5,858,006 A | 1/1999 | Van der AA et al. |
| 5,863,421 A | 1/1999 | Peter, Jr. et al. |
| 5,871,694 A | 2/1999 | Beden et al. |
| 5,895,368 A * | 4/1999 | Utterberg ................... 604/4.01 |
| 5,919,154 A | 7/1999 | Toays et al. |
| 5,951,870 A | 9/1999 | Utterberg |
| 6,004,302 A | 12/1999 | Brierley |
| 6,039,877 A | 3/2000 | Chavallet et al. |
| 6,042,784 A | 3/2000 | Wamsiedler et al. |
| 6,132,616 A * | 10/2000 | Twardowski et al. ........ 210/646 |
| 6,261,267 B1 | 7/2001 | Chen |
| 6,284,131 B1 | 9/2001 | Hagard et al. |
| 6,409,708 B1 | 6/2002 | Wessman |
| 6,474,375 B2 | 11/2002 | Spero et al. |
| 6,517,508 B1 * | 2/2003 | Utterberg et al. ........... 604/4.01 |
| 6,645,166 B2 | 11/2003 | Scheunert et al. |
| 6,649,063 B2 * | 11/2003 | Brugger et al. ............. 210/650 |
| 6,669,709 B1 | 12/2003 | Cohn et al. |
| 6,726,672 B1 | 4/2004 | Hanly et al. |
| 6,979,309 B2 | 12/2005 | Burbank et al. |
| 7,226,538 B2 | 6/2007 | Brugger et al. |
| 7,470,265 B2 | 12/2008 | Brugger et al. |
| 2002/0007137 A1 | 1/2002 | Utterberg et al. |
| 2004/0054321 A1 | 3/2004 | Schon et al. |
| 2004/0122418 A1 | 6/2004 | Voorhees |
| 2004/0186415 A1 | 9/2004 | Burbank et al. |
| 2005/0020958 A1 | 1/2005 | Paolini et al. |
| 2005/0045540 A1 | 3/2005 | Connell et al. |
| 2005/0061740 A1 | 3/2005 | Felding et al. |
| 2005/0065459 A1 | 3/2005 | Zhang et al. |
| 2005/0090774 A1 | 4/2005 | Tonelli et al. |
| 2005/0171469 A1 | 8/2005 | Cunningham |
| 2005/0209547 A1 | 9/2005 | Burbank et al. |
| 2005/0251086 A1 | 11/2005 | Sternby |
| 2005/0288623 A1 | 12/2005 | Hjatmarsson |

* cited by examiner

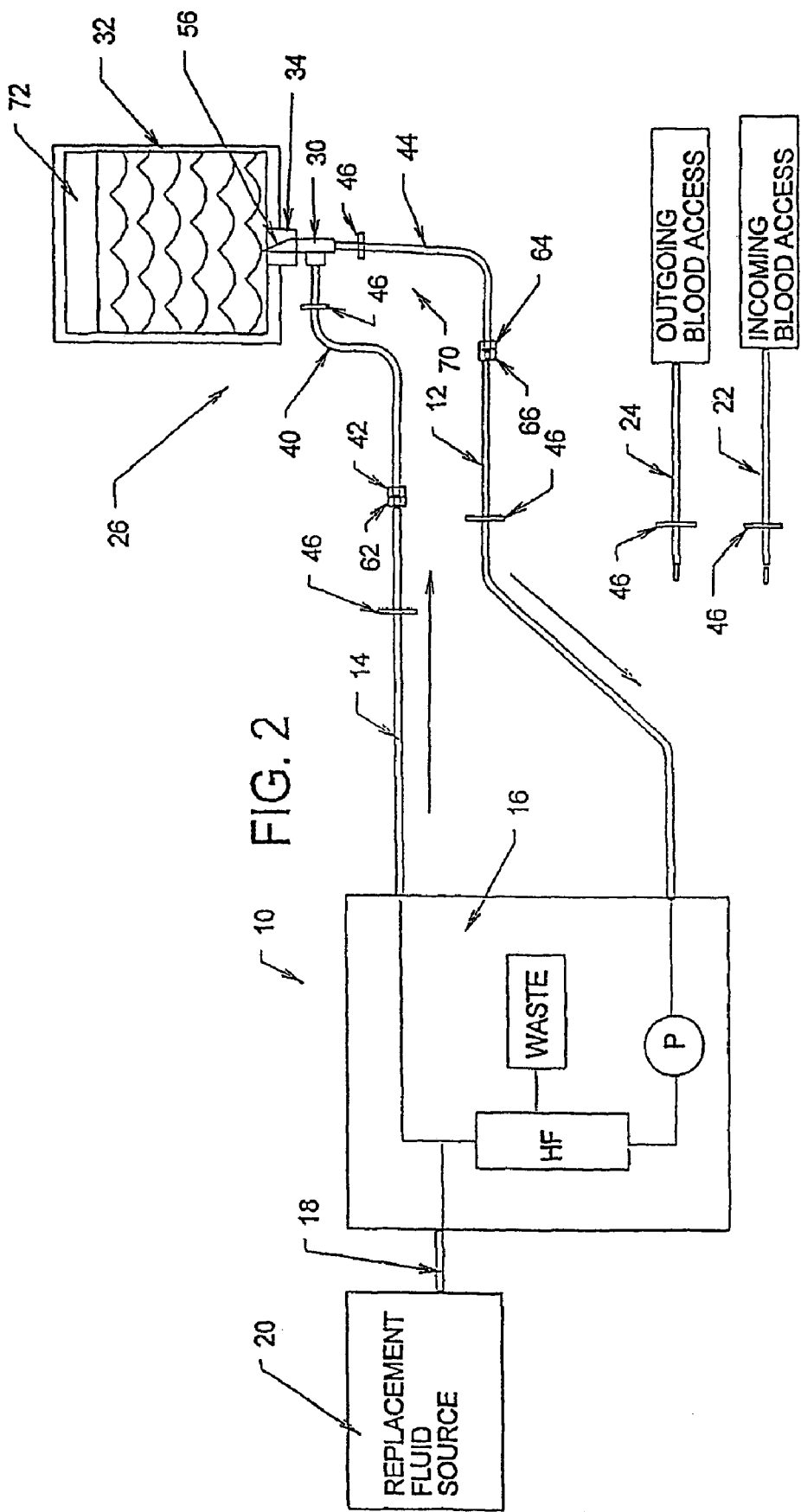

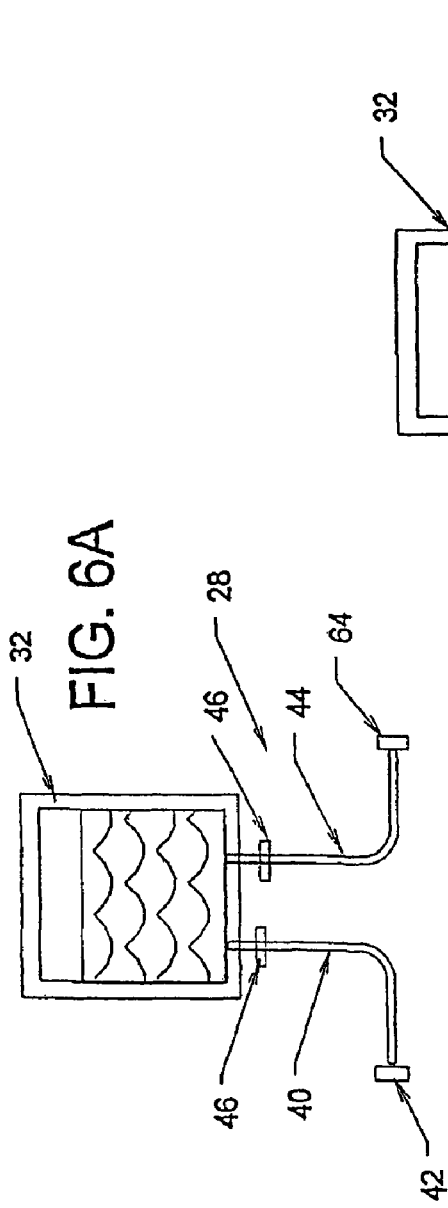
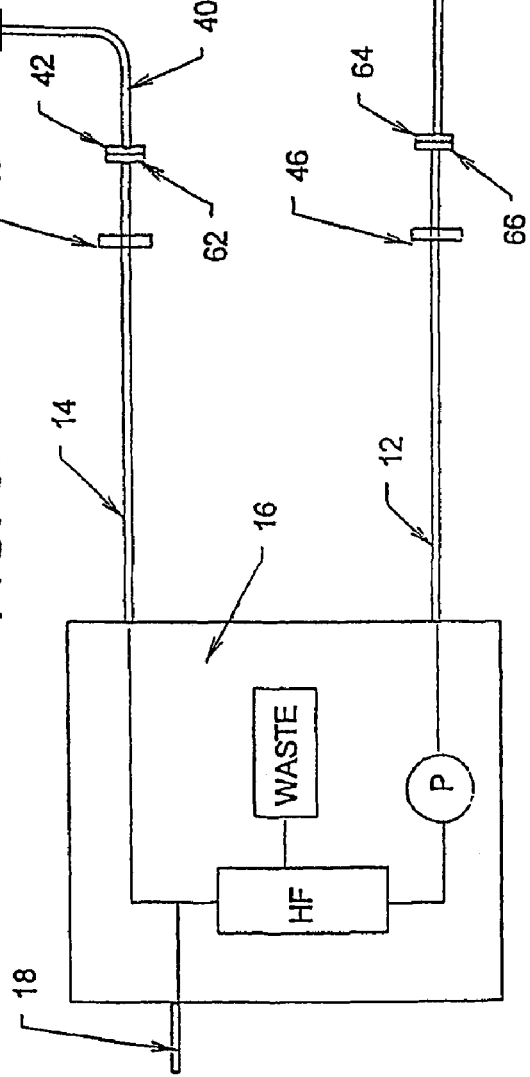

SYSTEMS AND METHODS FOR HANDLING AIR AND/OR FLUSHING FLUIDS IN A FLUID CIRCUIT

This application is a continuation of prior U.S. patent application Ser. No. 10/772,888, filed Feb. 4, 2004, now U.S. Pat. No. 7,226,538, which is a divisional of U.S. patent application Ser. No. 09/905,171, filed Jul. 13, 2001, now abandoned, the entireties of which are hereby incorporate by reference.

FIELD OF THE INVENTION

The invention generally relates to fluid processing systems and methods. In particular, the invention relates to systems and methods that process blood or fluids that are introduced into the body, for example, during filtration, dialysis, or other diagnostic or therapeutic purposes.

BACKGROUND OF THE INVENTION

Systems are well known that process or treat blood or other fluids, and that return processed or treated blood or fluids to an individual. It is necessary to eliminate air from such systems prior to and during use, to avoid introduction of air into the individual undergoing treatment. Typically, drip chambers are used. It is also desirable, after use, to flush residual blood or fluid from the system, typically for return to the individual undergoing treatment.

There remains a demand for straightforward ways to handle air and to rinse residual blood or fluids from blood or fluid processing systems.

SUMMARY OF THE INVENTION

The invention provides systems and methods for handling air in a fluid processing circuit. The invention also provides systems and methods for rinsing or flushing residual fluids from a fluid processing circuit after processing is concluded.

One aspect of the invention provides systems and methods for priming a fluid circuit. The systems and methods couple a connector assembly to a fluid reservoir. The connector assembly comprises a first fluid passage and a second fluid passage. The systems and methods circulate fluid in the fluid circuit through the fluid reservoir, by conveying fluid into the inlet of the fluid circuit from the reservoir through the second fluid passage while conveying fluid from the outlet of the fluid circuit into the reservoir through the first fluid passage. During the circulation step, the systems and methods accumulate air residing in the fluid circuit in the fluid reservoir, thereby removing air from the fluid circuit.

In one embodiment, the systems and methods releasably couple the first fluid passage to the outlet of the fluid circuit, and also releasably couple the second fluid passage to the inlet of the fluid circuit. In one arrangement, the systems and methods couple the first and second passages together in a loop after the accumulating step.

In one embodiment, the systems and methods convey fluid into the fluid reservoir at a higher gravity height than fluid is conveyed from the fluid reservoir.

Another aspect of the invention provides systems and methods for both priming and flushing a fluid circuit. The systems and methods provide a connector assembly comprising a first fluid passage that is releasably coupled to an outlet of the fluid circuit and a second fluid passage that is releasably coupled to an inlet of the fluid circuit. The systems and methods couple the connector assembly to a fluid reservoir. The systems and methods prime the fluid circuit through the fluid reservoir by conveying fluid into the inlet of the fluid circuit from the reservoir through the second fluid passage while conveying fluid from the outlet of the fluid circuit into the reservoir through the first fluid passage. After the priming step, the systems and methods release the coupling between the connector assembly and the inlet and outlet of the fluid circuit, while keeping the connector assembly coupled to the fluid reservoir. The systems and methods then process a selected fluid using the fluid circuit. After the processing step, the systems and methods couple the inlet of the fluid circuit to the second fluid passage. The systems and methods then rinse residue of the selected fluid from the fluid circuit by conveying fluid into the inlet of the fluid circuit from the reservoir through the second fluid passage, while conveying the selected fluid residue from the outlet of the fluid circuit in a path that bypasses the reservoir.

In one embodiment, during the processing step, the first and second fluid passages are coupled together in a loop.

Another aspect of the invention provides a fluid processing apparatus comprising a fluid container, and a connector assembly coupled to the fluid container. The connector assembly includes a first fluid passage that is releasably coupled by a luer connector to an outlet of a fluid circuit. The connector assembly also includes a second fluid passage that does not communicate with the first fluid passage and that is releasably coupled by a luer connector to a inlet of the fluid circuit. In this arrangement, fluid can be circulated by the connector assembly through the fluid container in a loop that includes the fluid circuit to collect in the fluid source air residing in the fluid circuit.

Regarding any above-discussed aspect of the invention, the connector assembly can, in one embodiment, comprise a single connector body that includes both the first and second fluid passages. In one arrangement, the connector body includes a distal end having a taper to form a spike, which can be coupled to the fluid reservoir, e.g., by penetrating a port tube membrane.

Regarding any above-discussed aspect of the invention, the connector assembly can comprise, in another embodiment, a first connector body that includes the first fluid passage and a second connector body that includes the second fluid passage. In one arrangement, each of the first and second connector bodies includes a distal end having a taper to form a spike, which can be coupled to the fluid reservoir, e.g., by penetrating a port tube membrane.

Another aspect of the invention provides a dual lumen connector for coupling to a fluid source. The connector comprises a body in which there are first and second fluid passages that do not communicate with each other. A first assembly communicates with the first fluid passage and includes a first fitting to releasably couple the first fluid passage to an outlet of a fluid circuit. A second assembly communicates with the second fluid passage and includes a second fitting to releasably couple the second fluid passage to an inlet of the fluid circuit. Using the connector, fluid can be circulated through the fluid source in a loop that includes the fluid circuit to collect in the fluid source air residing in the fluid circuit.

The fluid circuit used in association with the invention in all of its various aspects can itself take various forms and functions. The fluid circuit can, for example, comprise at least a portion of a hemofiltration system, or a hemodialysis system, or a hemodiafiltration system, or a peritoneal dialysis system.

The invention makes possible the use of fluid circuits free of drip chambers, thereby minimizing the quantity of priming fluid discarded during priming.

Other features and advantages of the inventions are set forth in the following specification and attached drawings.

BRIEF DESCRIPTION OF THE DRAWINGS

FIG. 2. is a schematic view of a priming system that can be used with the fluid processing system shown in FIG. 1, which includes a dual lumen connector assembly;

FIG. 6A is a schematic view of an alternative fluid priming assembly comprising a priming container with integrally connected first and second tubing assemblies that can be used with the fluid processing system shown in FIG. 1;

FIG. 6B is a schematic view of a system formed after connecting the fluid priming assembly shown in FIG. 6A with the fluid circuit shown in FIG. 1;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENT

I. System Overview

Figure 1:
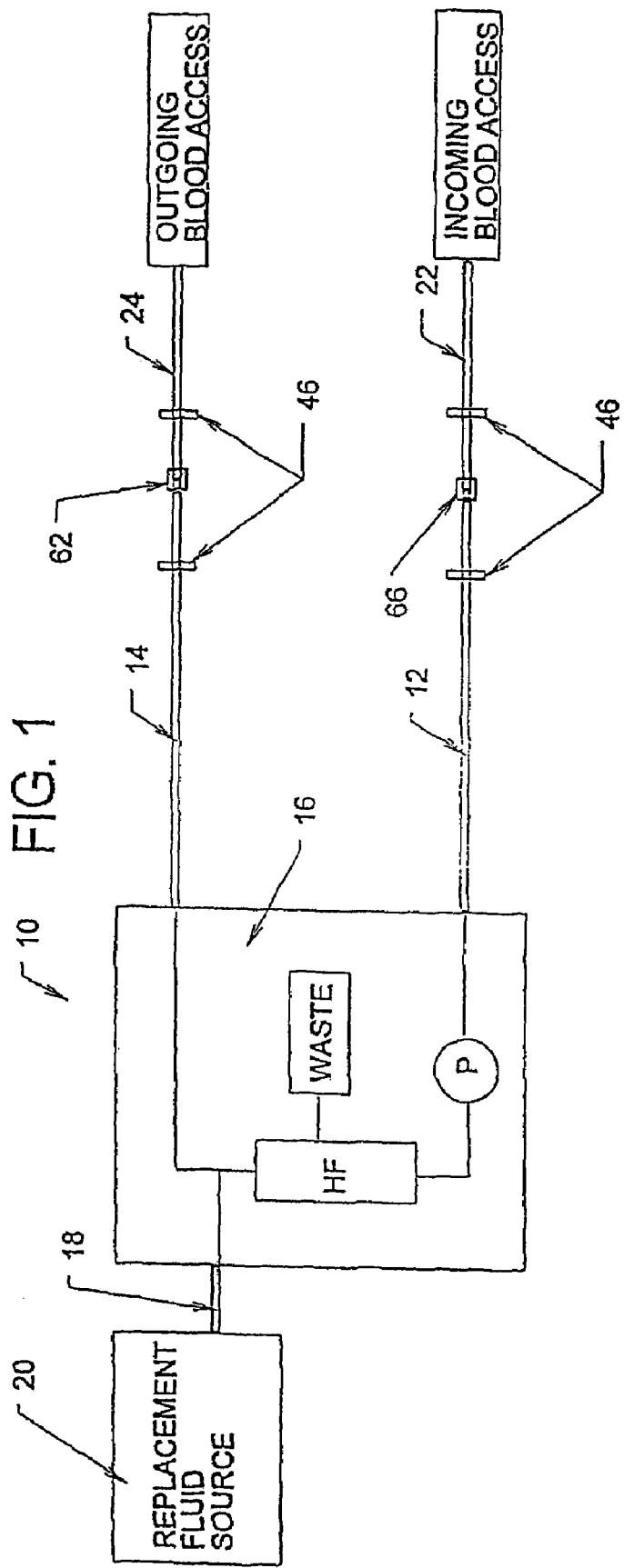
FIG. 1 is a schematic view of a generic fluid processing system.

FIG. 1 schematically shows the components of a generic fluid processing system 10. The system 10 has a first inlet 12 for receiving fluid and an outlet 14 for discharging fluid. A fluid circuit 16 is coupled between the first inlet 12 and the outlet 14, through which the incoming fluid flows and is then discharged. The fluid circuit 16 processes the fluid in a desired manner and can be conventional.

The fluid circuit 16 may also include a second inlet 18 through which a processing fluid is introduced into the fluid circuit 16. The processing fluid is drawn from a source 20, which can be fluid containers or a sterile fluid generating source. The sterile fluid can be generated, e.g., by treating water from an external source, or by sterile filtering a fluid waste product of the fluid circuit 16 itself, e.g., as disclosed in application Ser. No. 09/027,301 filed Feb. 19, 1998 and entitled "Hemofiltration System Including Ultrafiltrate Purification and Reinfusion System," which is incorporated herein by reference.

The fluid processing system 10 can take various forms. It can, for example, comprise a blood processing system for conducting hemofiltration, or hemodialysis, or hemodiafiltration. The system 10 can also comprise a peritoneal dialysis system.

As will be described herein for purpose of illustration, the system 10 forms a part of a hemofiltration system. The system receives through the first inlet 12 blood from an individual, e.g., through a suitable incoming blood line 22, which can comprise an access site for withdrawing blood from an individual, e.g., by connection to an artery, a vein, or a fistula. An in-line pinch clamp 46 or the like can be provided in the blood line 22. A pumping mechanism P in the fluid circuit 16 pumps the blood through a hemofilter HF, where toxins (WASTE) are removed. The treated blood is discharged through the outlet 14 for return to the circulatory system of the individual, e.g., through a suitable outgoing blood line 24, which can comprise an access site for returning blood to an individual,. e.g., typically by connection to a vein. An in-line pinch clamp 46 or the like can also be provided in the blood line 24.

During hemofiltration, a replacement fluid is typically added to the treated blood through the second inlet 18, to make up for the fluid lost during toxin removal. Typically, the replacement fluid is added in volumetric proportion to the amount of fluid removed from the blood. The replacement fluid is drawn from the source 20, which communicates with to the second inlet 18.

As is the case before using many fluid processing systems, it is necessary before conducting hemofiltration to remove residual air from the fluid circuit 16 and, after conducting hemofiltration, to rinse blood and residual fluid from the fluid circuit 16.

Accordingly, the system 10 includes a fluid priming assembly 26 (shown in FIGS. 2; 3A/B/C; and 4). The purposes of the fluid priming assembly 26 are (1) to prime the system and thereby remove residual air from the fluid circuit 16 prior to use, and (2) to "rinse back" or flush residual blood from the fluid circuit 16 after use.

Further details of the fluid priming assembly 26 will now be described.

II. The Fluid Priming Assembly

A. Priming Function

Details of the fluid priming assembly 26 are illustrated in FIGS. 2; 3A/B/C; and 4).

Figure 3A:
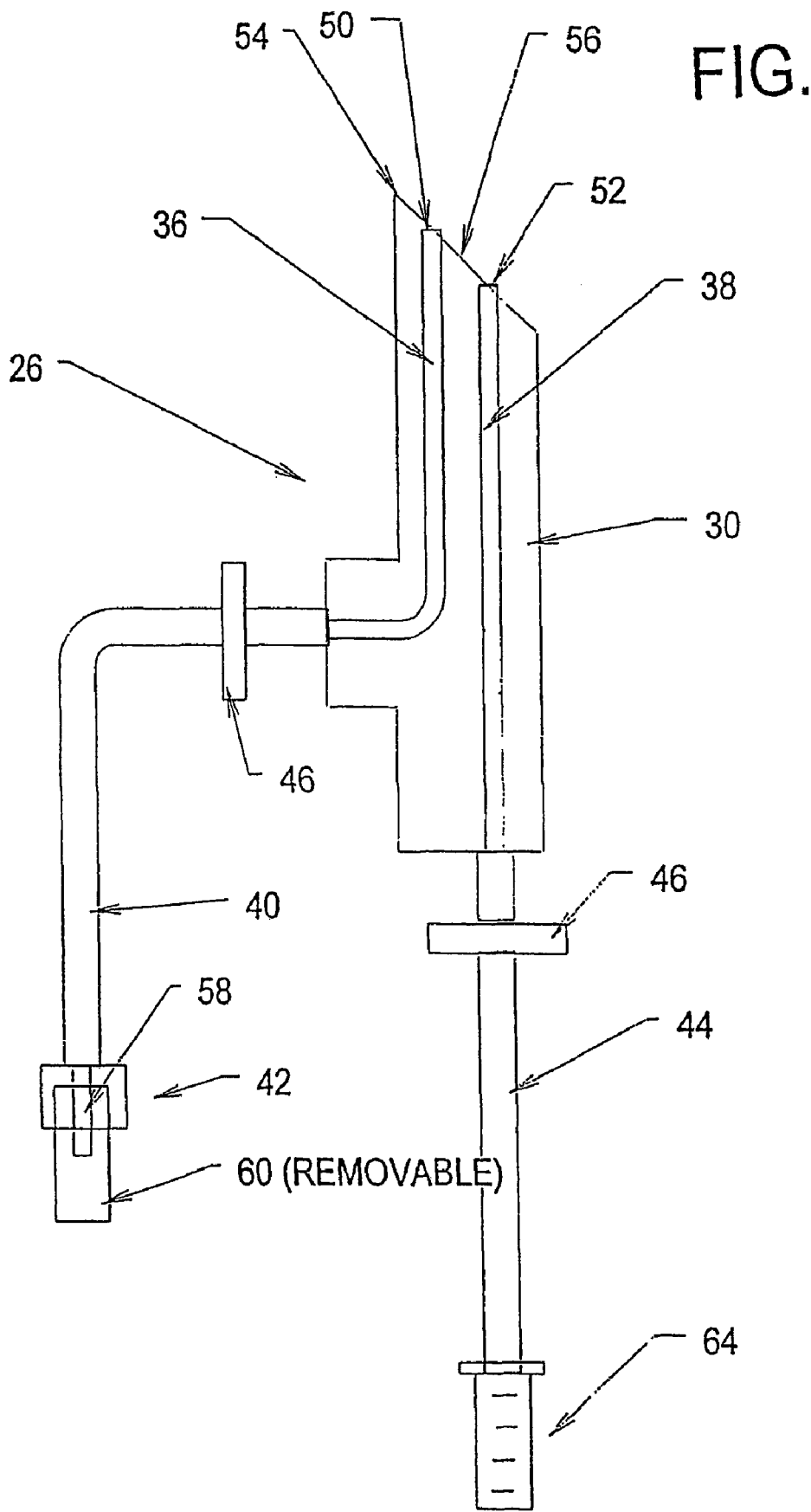
FIG. 3A is an enlarged side sectional view of the dual lumen connector assembly that forms a part of the priming system shown in FIG. 2.

As there shown, the fluid priming assembly 26 includes a connector 30 formed, e.g., from hard, medical grade plastic. There are two fluid passages (lumens) 36 and 38 (see FIG. 3A) formed in the body of the connector 30. These passages 36 and 38 can be formed, e.g., by conventional molding techniques. These passages 36 and 38 are discrete, such that the second fluid passage 38 does not communicate with the first fluid passage 36 within the body of the connector 30.

In use, the connector 30 is intended to be coupled in fluid communication with a container 32 of priming solution. The priming container 32 can comprise, e.g., flexible bag containing saline or other suitable priming solution. In use, the priming container 32 is positioned above the fluid circuit 16. Alternatively, the processing fluid source 20 can also be used as the source of priming solution.

The connector 30 may be coupled to the priming container 32 in various conventional ways, e.g., through a luer fitting or by penetration of a port tube membrane 34. In the illustrated embodiment (see FIG. 3B), the priming container 32 includes a port tube membrane 34. In this arrangement, the tip end of the connector 30 is tapered to form a spike 56, providing a configuration similar to vented-type spikes for rigid bottles. In the illustrated embodiment (see FIG. 3A), the opening 50 of the first fluid passage 36 into the container 32 is located closer to the high tapered end 54 of the spike 56 than the opening 52 of the second fluid passage 38 into the container 32. Thus, the first fluid passage 36 enters the container 32 at a higher gravity position than the second fluid passage 38. The benefits of this configuration will be discussed later.

The fluid priming assembly 26 includes a first flexible tubing assembly 40 (see FIG. 3A) coupled to the connector 30. The first tubing assembly 40 communicates only with the first fluid passage 36. The first tubing assembly 40 terminates with a connector 42 to releasably connect the first fluid passage 36 to the fluid circuit 16. The connector 42 can take various forms, depending upon the configuration of the mating connector in the fluid circuit 16. In the illustrated embodiment, the connector 42 comprises a male luer 58 with a removable female-to-female connector 60 carried by the male luer 58. The removable connector 60 carried by the male luer 58 is adapted to be coupled to a mating male connector 62 on the outlet 14 of the the fluid circuit (as FIG. 2 shows). In use (see FIG. 3B), priming fluid and residual air in the fluid circuit 16 is pumped by way of the first tubing assembly 40, into the first fluid passage 36 and into the priming container 32.

The fluid priming assembly 26 includes a second flexible tubing assembly 44 (see FIG. 3A) coupled to the connector 30. The second tubing assembly 44 communicates only with the second fluid passage 38. The second tubing assembly 44 terminates with a connector 64 to releasably connect the second fluid passage 36 to the fluid circuit 16. The connector 64 can take various forms, depending upon the configuration of the mating connector in the fluid circuit 16. In the illustrated embodiment, the connector 64 comprises a female luer connector that is adapted to be coupled to a mating male connector 66 on the inlet 12 of the fluid circuit (see FIG. 2). In use (see FIG. 3B), vented fluid (free of air) is conveyed by way of the second tubing assembly 44 into the fluid circuit 16, from the priming container 32 into the second fluid passage 38.

Figure 3B:
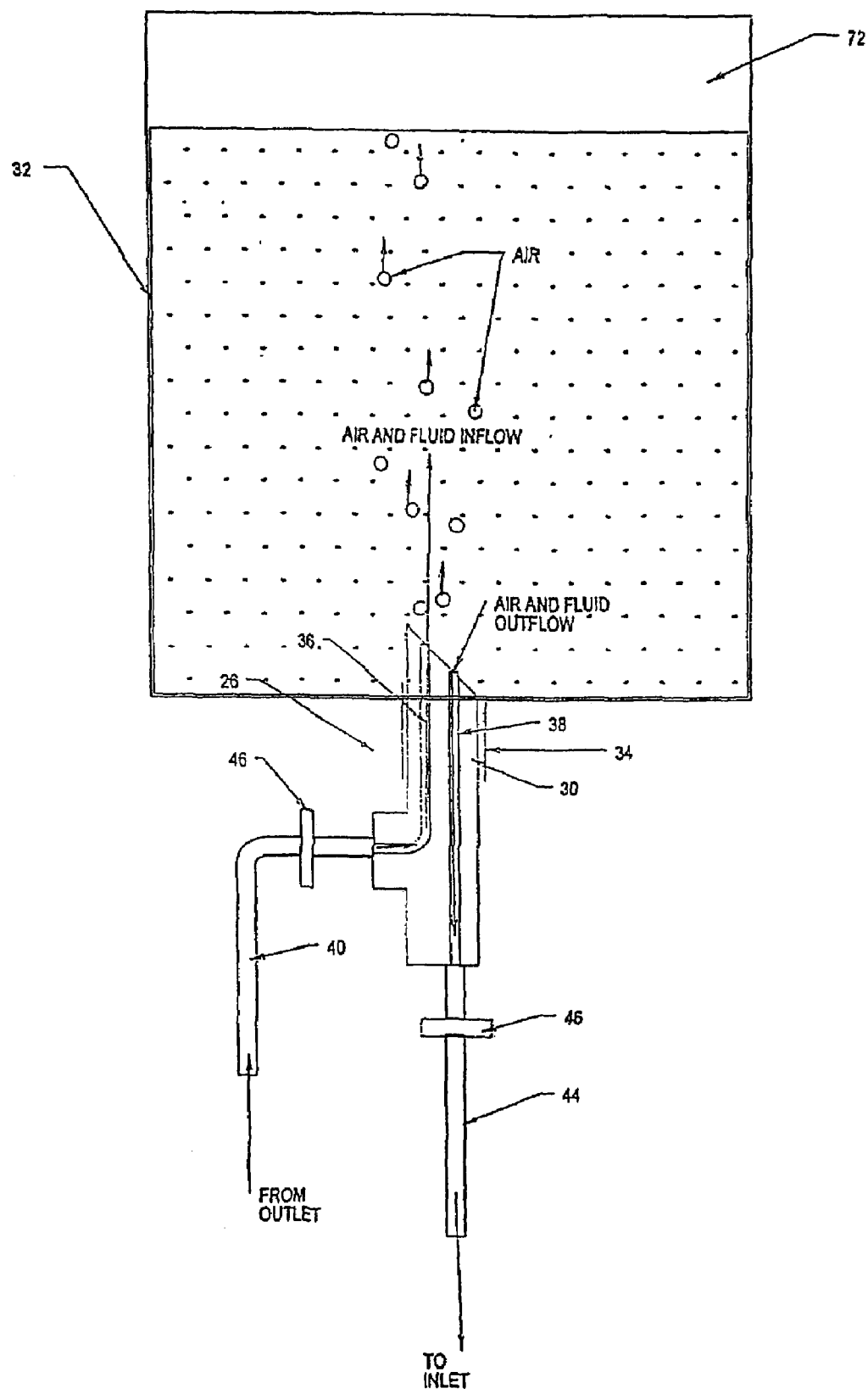
FIG. 3B is an enlarged side sectional view of the dual lumen connector assembly shown in FIG. 3A when performing a priming function.
Figure 3C:
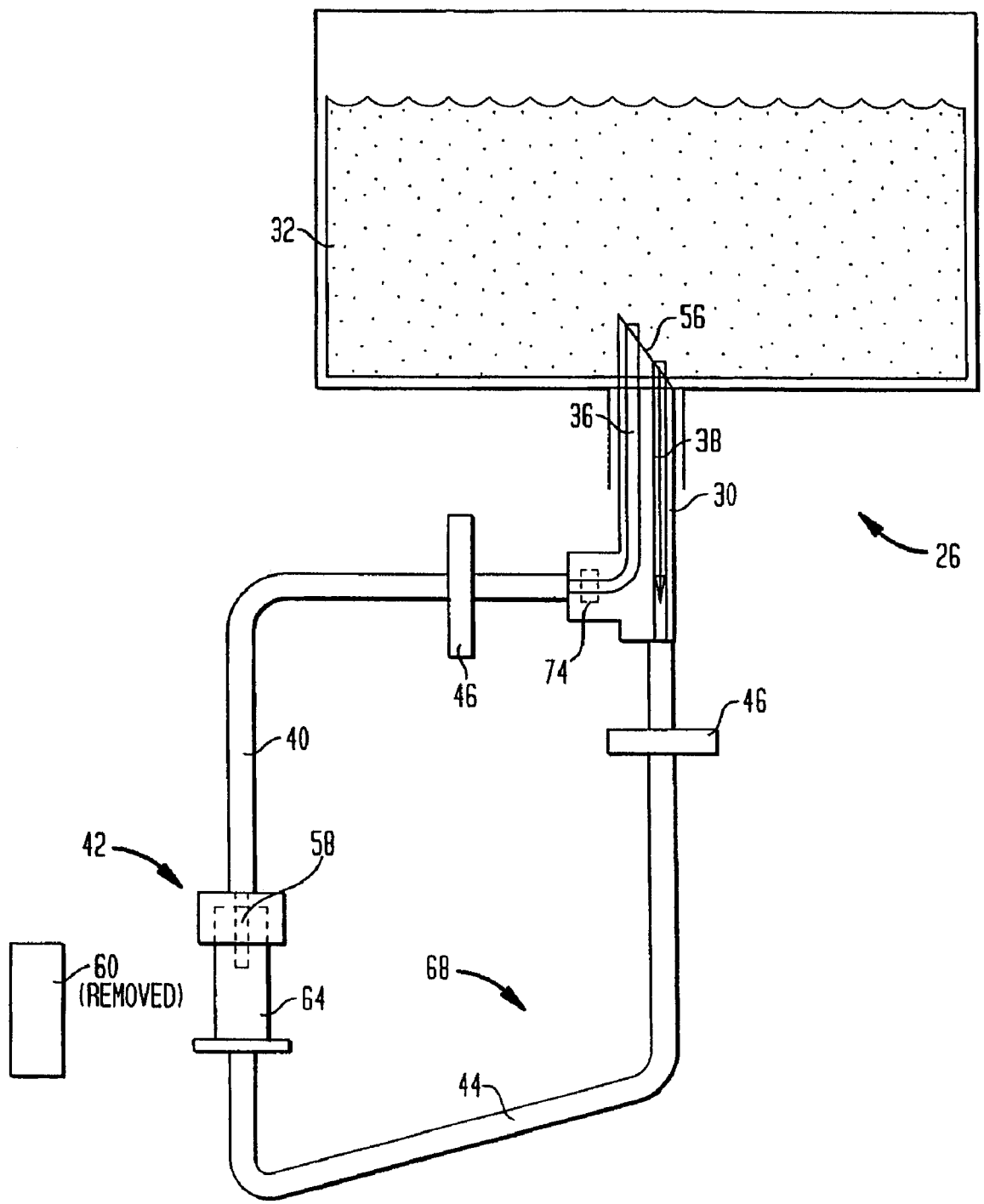
FIG. 3C is an enlarged side sectional view of the dual lumen connector assembly shown in FIG. 3A formed into a closed loop that preserves its sterility after performing the priming function shown in FIG. 3B and before performing a rinse-back function.

Desirably, the connectors 42 and 64 are configured to also enable their connection one to the other in a sterile fashion (see FIG. 3C). In this way, after disconnection from the fluid circuit 16, the first and second tubing assemblies 40 and 44 can be coupled together to form a closed loop 68, to maintain sterility after being used to perform a priming function, so that additional functions, e.g., a rinse-back function, can be performed using the same connector 30 and priming container 32. Further details of this feature will be described later.

With the first and second tubing assemblies 40 and 44 coupled to the fluid circuit 16 in the manner shown in FIG. 2, the connector 30 forms a priming loop 70 that circulates the priming solution through both the priming container 32 and the fluid circuit 16. Conventional pinch clamps 46 are provided on both the first tubing assembly 40 and the second tubing assembly 44, as well as the inlet and outlet 12 and 14. These pinch clamps 46 allow regulation and control of fluid flow through the priming loop 70 and fluid circuit 16.

As FIG. 3B shows, priming solution is drawn (by the fluid circuit pump P in the inlet line 12) through the second tubing assembly 44 from the priming container 32 and into the fluid circuit 16. Residual air occupying the fluid circuit 16 is displaced by the priming solution and returned with the priming solution through the first tubing assembly 40 back into the priming container 32. Because the opening 50 of the first fluid passage 36 (conveying air and fluid into the container 32) is located at a higher gravity height than the opening 52 of the second fluid passage 38 (conveying fluid out of the container 32), air in the fluid outflow discharged by the first fluid passage 36 is not drawn or sucked into the fluid inflow entering the second fluid passage 38. Instead, the air floats upward, away from the second fluid passage 38 and is collected in the air space 72 at the top of the container 32. This permits the fluid circuit 16 to be primed with fluid contained in the priming container 32, while virtually all air is expelled from the fluid circuit 16 and trapped in the air space 72 in the priming container 32. This procedure removes all air from the system 10.

The pump P may continue to operate in this fashion until steps are taken to begin fluid processing. For example, when the fluid circuit 16 is being used to conduct hemofiltration, the pump P can be operated to continuously recirculate the priming fluid from the container 32 through the circuit 16. until the patient is available for attachment to the fluid circuit 16.

Figure 5:
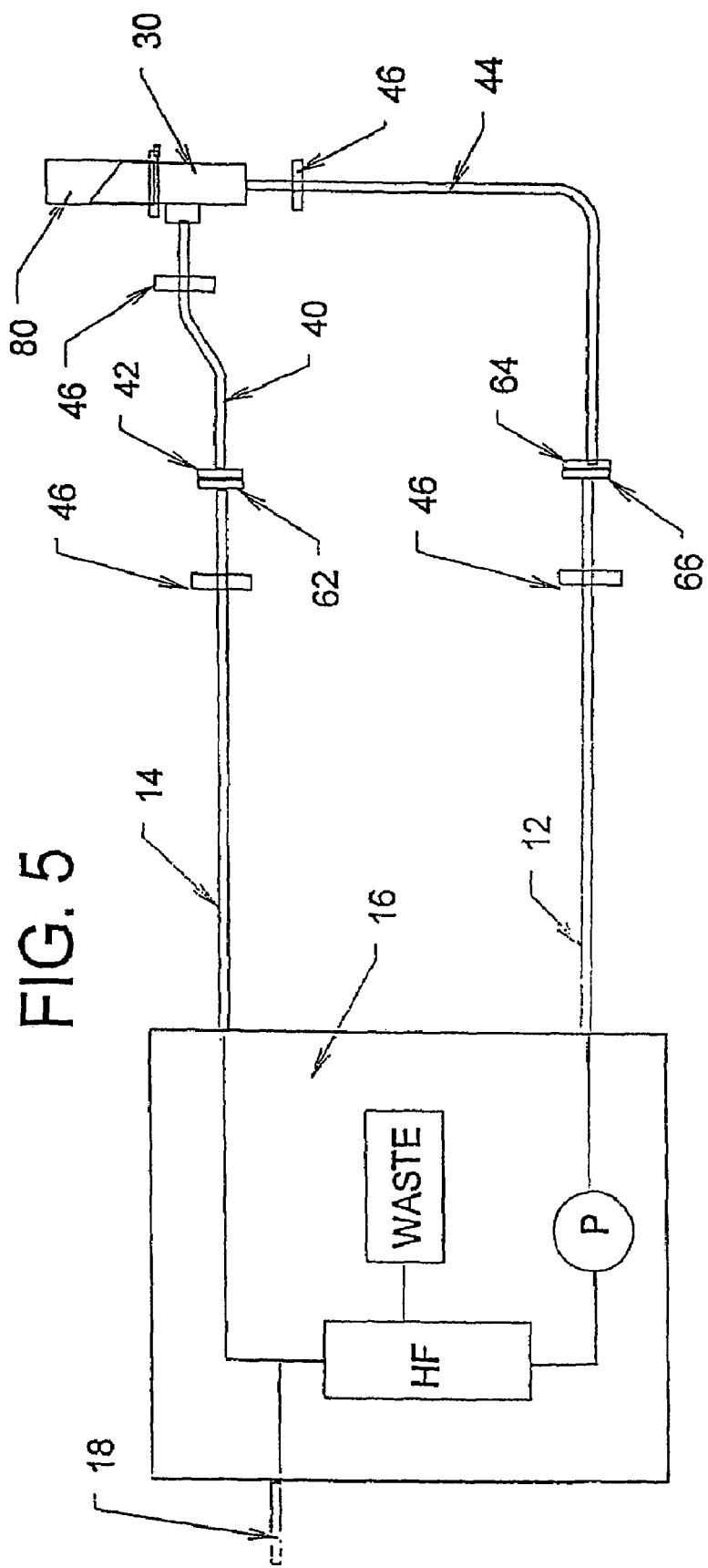
FIG. 5. is a schematic view of a system with a dual lumen connector assembly as shown in FIG. 3A, which is supplied to an operator preconnected to a fluid circuit.

In a preferred embodiment (see FIG. 5), the fluid circuit 16 is supplied to the operator with the connector 30 releasably preconnected to the circuit 16 by the connectors 66/64 and 62/42. In this arrangement, the connector 30 is enclosed in a sterile manner within a cap 80, which maintains its sterility prior to use. When supplied to the operator, the pinch clamps 46 provided upstream and downstream of the connectors 66/64 and 62/42 are preferably open.

Priming of the fluid circuit 10 commences with the removal of the cap 80 and coupling the connector 30 to the priming container 32 (see FIG. 2). The pump P is operated in a forward flow condition to draw fluid from the priming container 32 and push air into the priming container 32 (as shown in FIG. 3B). The priming solution is circulated in this manner in the loop 70 until priming solution fills the fluid circuit 16 and all air is expelled and collected in the air space 72 at the top of the priming container 32.

A flow restrictor 74 can be placed in the first tubing assembly 40 or in the first fluid passage 36. The flow restrictor 74 helps to create a positive back pressure at the outlet 14, to facilitate complete priming of the hemofilter HF (or other blood processing device the system 10 may incorporate).

Once the fluid circuit 16 is primed, operation of the pump P is terminated, and all pinch clamps 46 are closed. The operator disconnects the connector 62 from the connector 42. The free connector 62 on the outlet 14 is, in turn, coupled to the outgoing fluid access line 24. While the connection of the outlet 14 to the outgoing fluid access line 24 occurs, the female-to-female connector 60 is left attached to the male luer 58 of the connector 42, to serve as a cap for the male luer 58. As a cap, the connector 60 covers the male luer 58 on the first tubing assembly 40, to maintain its sterility while the inlet 12 of the fluid circuit 16 is disconnected from the second tubing assembly 44.

To disconnect the inlet 12 of the fluid circuit 16 from the second tubing assembly 44, the operator disconnects the connector 66 from connector 64. The free connector 66 on the inlet 12 is, in turn, coupled to the incoming fluid access line 22. The system 10 is now in the condition for use shown in FIG. 1.

The female-to-female connector 60 is now removed to expose the male luer 58 of the first tubing assembly 40. The connector 60 can now be discarded. The male luer 58 can then be connected with the female luer 64 on the second tubing assembly 44 (see FIG. 3C). The closed loop 68 is thereby formed between the first and second tubing assemblies 40 and 44, through the priming container 32, to maintain sterility within the connector 30 and tubing assemblies 40 and 44 until the rinse-back function is performed. When the closed loop 68 is formed, the clamps 46 in the tubing assemblies 40 and 44 may be closed.

The clamps 46 on inlet and outlet lines 12 and 14 and the incoming and outgoing fluid access lines 22 and 24 can be opened. Operation of the pump P begins, and the primed fluid circuit 16 processes blood and fluid in the desired manner (e.g., hemofiltration).

B. Rinse-Back Function

Figure 4:
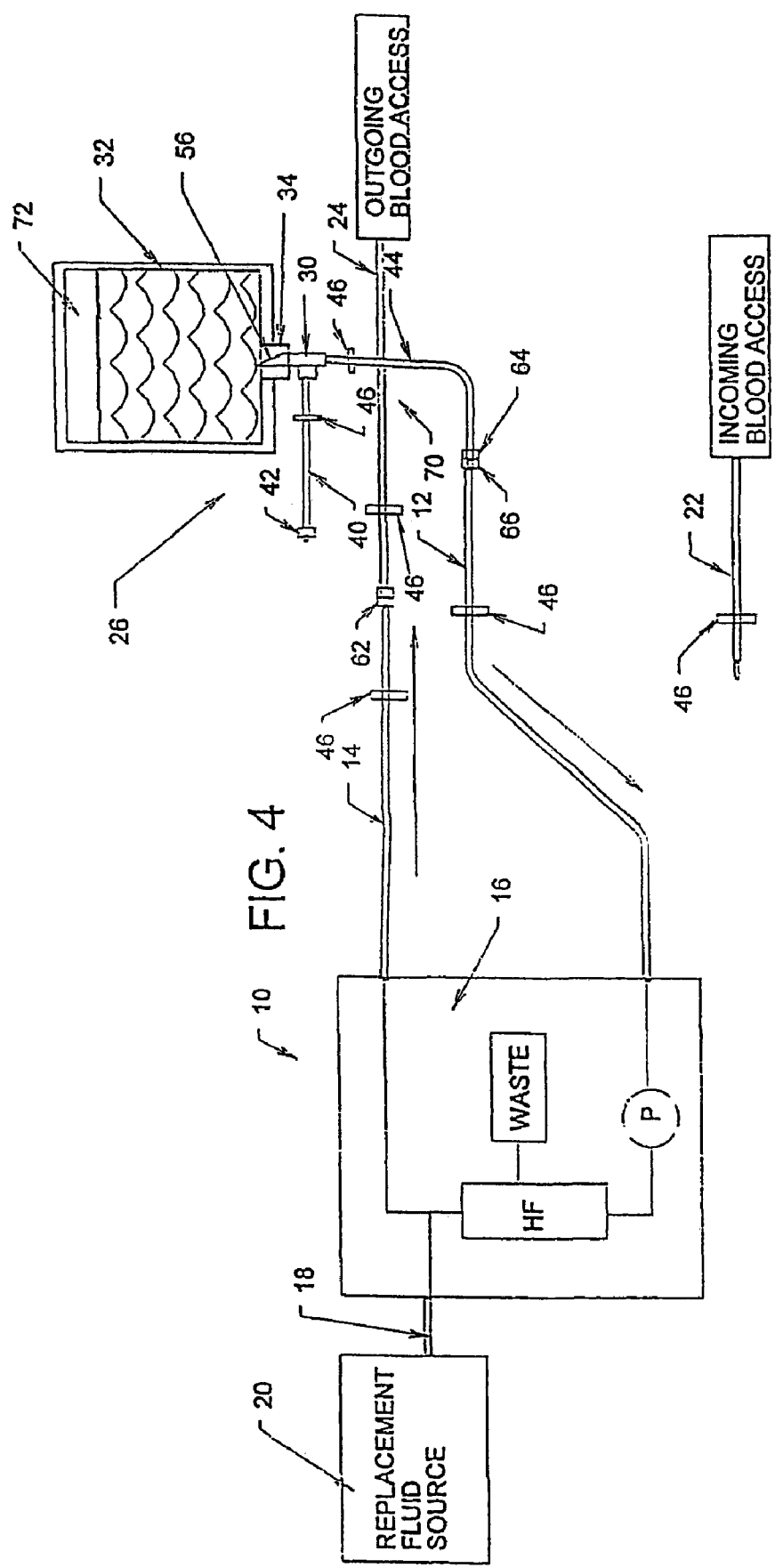
FIG. 4. is a schematic view of a rinse-back system that can be used with the fluid processing system shown in FIG. 1, and which includes the same dual lumen connector assembly that previously performed the priming function shown in FIG. 3B.

The rinse-back function is performed at the end of the blood processing session. The rinse-back function is illustrated in FIG. 4.

After blood processing, the outgoing fluid access assembly 24 is left connected to the outlet 14, to return residual fluid from the fluid circuit 16 to the individual during the rinse-back function. The operator disconnects the male luer 58 on the first tubing assembly 40 from the female luer 64 on the second tubing assembly 44, to interrupt the loop 58. The clamps 46 on the incoming fluid access assembly 22 and inlet 12 are closed. The incoming fluid access assembly 22 is disconnected from the inlet 12. The female luer 64 of the second tubing assembly 44 is coupled to male luer 66 on the inlet 12.

The pinch clamps 46 in the second tubing assembly 44 and the inlet 12 are opened (the pinch clamp 46 on the first tubing assembly 40 remains closed). Subsequent operation of the pump P draws priming solution from the container 32 into and through the fluid circuit 16. In this process, residual blood remaining in the fluid circuit 16 is effectively rinsed or flushed from the circuit 16 and ultimately returned to the individual through the outgoing fluid access assembly 24. This reduces the amount of blood loss by the individual.

At the end of the rinse-back function, the operator disconnects the outlet 14 from the outgoing fluid access assembly 24. The system 10, which includes the fluid circuit 16 connected by the connector 30 to the priming container 32, can now be discarded as a unit.

The arrangement as described performs both a priming function and a rinse back function using the same connector assembly and the same source of solution.

III. Other Embodiments

The fluid priming assembly 26 can be constructed in various alternative ways.

For example, as shown in FIG. 6A, a fluid priming assembly 28 comprises the priming container 32 that is supplied to the operator with the first and second tubing assemblies 40 and 44 attached as individual lengths of flexible tubing integrally coupled directly to priming container 32, without use of the intermediate dual lumen connector 30. Each tubing length 40 and 44 includes its own luer connector, respectively 42 and 64, and an upstream pinch clamp 46, which is closed at the time it is supplied to the operator. At time of use (as FIG. 6B shows), the first tubing assembly connector 42 can be coupled the connector 62 of the outlet 14, and the second tubing assembly connector 64 is coupled to the connector 66 of the inlet 12. Alternatively, the container 32 with preconnected first and second tubing assemblies can be supplied to the operator releasably preconnected to the fluid circuit 16 in the manner shown in FIG. 6B.

Once the components are assembled as shown in FIG. 6B, the pinch clamps 46 can be opened and the pump P operated in the manner as previously discussed, to draw fluid from the priming container 32 and push air into the priming container 32, thereby priming the fluid circuit 16. Subsequent manipulation of the first and second tubing assemblies 40 and 44 and priming container 32, to enable fluid processing in the fluid circuit 16 after priming, as well as to conduct a rinse back function after fluid processing, is carried out in the same manner as discussed with regard to the configuration shown in FIG. 5.

Figure 7:
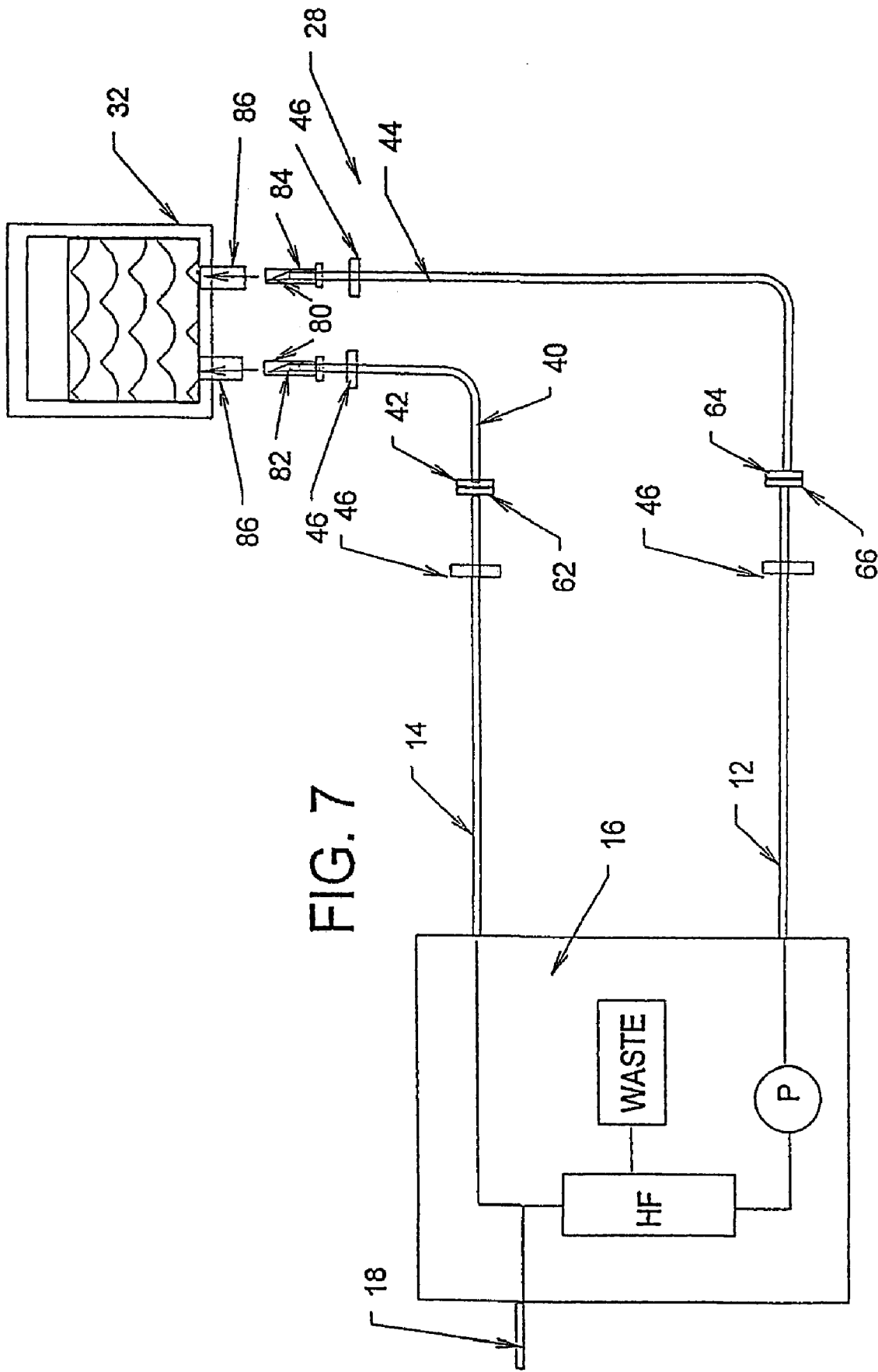
FIG. 7 is a schematic view of an alternative embodiment of a fluid priming assembly, which is supplied to an operator preconnected to a fluid circuit.

Alternatively, as shown in FIG. 7, a fluid priming assembly 28 comprises the first and second tubing assemblies 40 and 44 taking the form of individual lengths of flexible tubing coupled directly to priming container 32 at time of use by means of separate connectors 82 and 84. The connectors 82 and 84 can take the form of luer fittings or, as shown in FIG. 7, spikes that penetrate separate port tube membranes 86 on the priming container 32. As FIG. 7 shows, the two connectors 82 and 84 (desirably enclosed within caps 80) can be supplied to the operator releasably preconnected to the circuit 16 by the connectors 66/64 and 62/42, in the same manner as the single connector 30 shown in FIG. 5. After coupling the dual connectors 82 and 84 to the priming container 32 at time of use (as indicated by arrows in FIG. 7), the manipulation of the first and second tubing assemblies 40 and 44 in FIG. 7 to carry out the priming and rinse back functions is the same as discussed with regard to the single connector configuration shown in FIG. 5.

Figure 8:
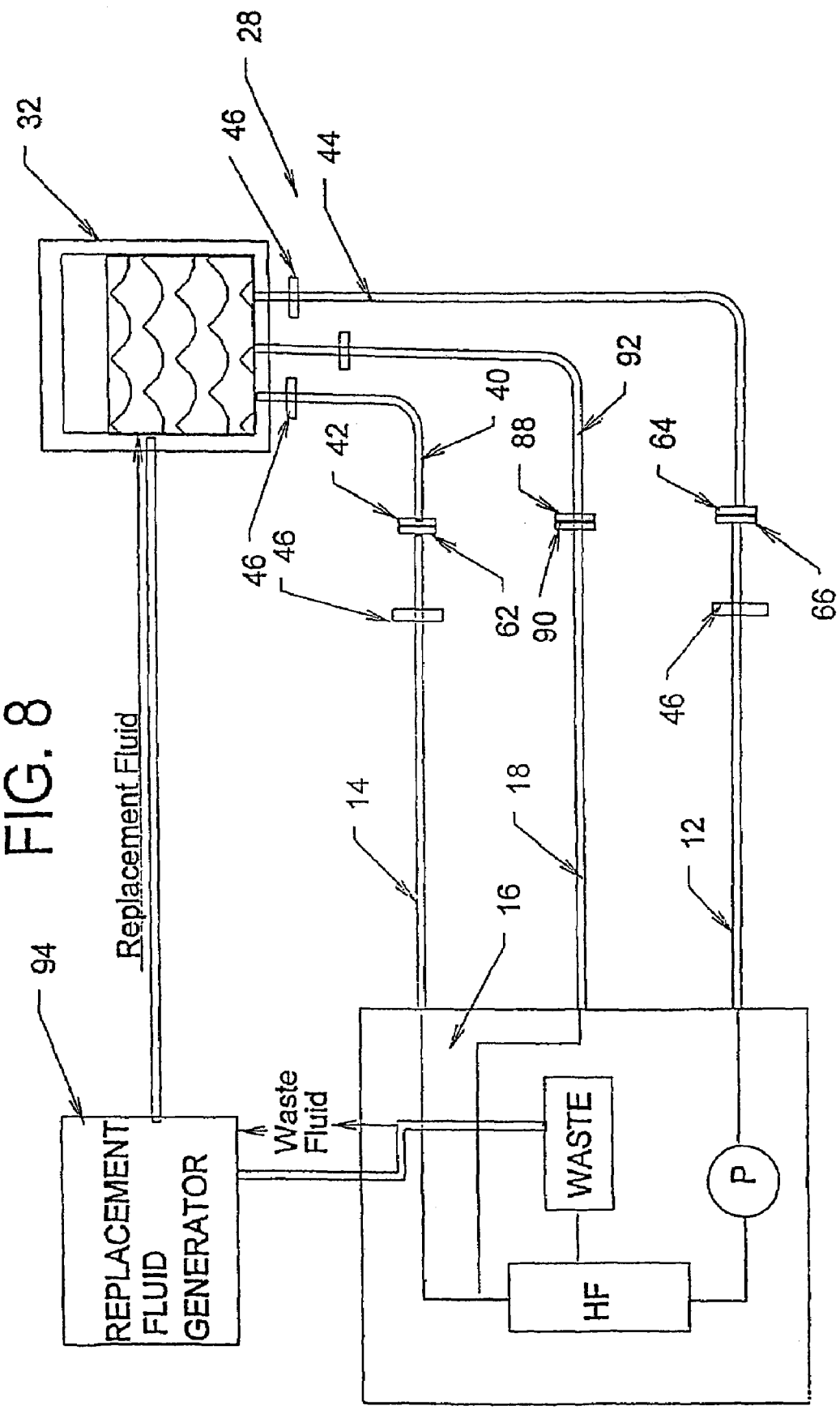
FIG. 8 is a schematic view of a container that carries replacement fluid and that includes both an associated fluid priming assembly and replacement fluid inlet path.

In another alternative embodiment (see FIG. 8), the fluid that the container 32 carries can comprise the replacement fluid that is added to make up for fluid lost during toxin removal. In this arrangement, the inlet 18 includes a connector 90 that releasably couples to a mating connector 88 carried by a third tubing assembly 92, which is itself coupled directly to the container 32. The third tubing assembly 92 can be coupled to the container 32 in the same manner as the first and second tubing assemblies 40 and 44, i.e., either by integral coupling or by use of instant-of-use luer or spike connectors. In this arrangement, the tubing assemblies 40 and 44 convey the replacement fluid to perform a priming and rinse back function at the beginning and end of fluid processing, as previously described, while the third tubing assembly 92 conveys replacement fluid during fluid processing. In this arrangement, the container 32 can comprise a container prefilled with replacement fluid, or it can comprise a reservoir that receives replacement fluid from a sterile fluid generating source during fluid processing. The sterile fluid can be generated, e.g., by treating water from an external source or (as FIG. 8 shows) by sterile filtering the fluid waste product of the fluid circuit 16 itself in a replacement fluid generation device 94, e.g., of a type disclosed in application Ser. No. 09/027,301 filed Feb. 19, 1998 and entitled "Hemofiltration System Including Ultrafiltrate Purification and Reinfusion System," which is incorporated herein by reference.

Features and advantages of the invention are set forth in the following claims.

We claim:

1. A fluid processing system comprising:

a fluid circuit including a filter with a membrane;

the fluid circuit further including blood and non-blood circuits separated from each other by the membrane;

the blood circuit having an inlet and an outlet connected to a connector assembly, the connector assembly including a first fluid passage coupled to the outlet of the fluid circuit and a second fluid passage that does not communicate with the first fluid passage and is coupled to the inlet of the fluid circuit, the first and second fluid passages being housed in a common assembly constructed for coupling to a container, which is filled with sterile fluid and serves as a fluid source, so as to form a loop such that fluid is circulated by the connector assembly through the container in the loop, thereby collecting in the container air residing in the blood circuit, at least a portion of the loop including the blood circuit from the inlet to the outlet, wherein the membrane is arranged at a portion of the blood circuit between the blood circuit inlet and the blood circuit outlet.

2. The system of claim 1, wherein said filter includes a hemofilter to remove toxins from blood.

3. A system according to claim 1, wherein the fluid circuit comprises at least a portion of a hemofiltration system.

4. A system according to claim 1, wherein the fluid circuit comprises at least a portion of a hemodialysis system.

5. A system according to claim 1, wherein the connector assembly is releasably coupled to the fluid container.

6. A fluid processing system comprising:

a fluid circuit including a blood circuit, a non-blood circuit, and a filter with a membrane separating the blood and non-blood circuits, the blood circuit having a blood circuit inlet and a blood circuit outlet; and a connector configured for coupling to a container filled with sterile fluid so as to provide fluid from the container to the blood circuit, the connector having a first inlet, a first outlet, a second inlet, and a second outlet, the first inlet connected to the first outlet so as to define a first fluid passage within the connector, the second inlet connected to the second outlet so as to define a second fluid passage that does not communicate with the first fluid passage within the connector, the blood circuit inlet connected to the connector first inlet, the blood circuit outlet connected to the connector second inlet, wherein at least a portion of a loop is formed between the connector first inlet and the connector second outlet and includes the blood circuit, and the fluid processing system is configured such that fluid from the container is circulated through the loop so that any air residing in the blood circuit is collected in the container when the connector is coupled to the container.

7. The fluid processing system of claim 6, wherein the filter includes a hemofilter to remove toxins from blood.

8. The fluid processing system of claim 6, wherein the fluid circuit comprises at least a portion of a hemofiltration system.

9. The fluid processing system of claim 6, wherein the fluid circuit comprises at least a portion of a hemodialysis system.

10. The fluid processing system of claim 6, wherein the connector is releasably coupled to the container.

11. The fluid processing system of claim 6, further comprising a pump.

12. The fluid processing system of claim 6, wherein the blood circuit inlet and blood circuit outlet are adapted to be disconnected from the connector and connected to arterial and venous blood lines, respectively.

13. The fluid processing system of claim 6, wherein the connector has a tip end tapered to form a spike, and the connector first inlet and the connector second outlet are disposed proximal the tip end.

14. A fluid processing apparatus comprising:

a fluid circuit including a blood circuit, a non-blood circuit, and a filter with a membrane separating the blood and non-blood circuits, the blood circuit having a blood circuit inlet and a blood circuit outlet;

a fluid container; and a connector coupled to the fluid container, the connector including a first fluid passage releasably coupled to the blood circuit outlet and a second fluid passage, which does not communicate with the first fluid passage, releasably coupled to the blood circuit inlet, wherein fluid from the container is circulated through the connector in a closed loop that includes the blood circuit and the container so as to collect in the container air residing in the blood circuit.

15. The fluid processing apparatus of claim 14, wherein the filter includes a hemofilter to remove toxins from blood.

16. The fluid processing apparatus of claim 14, wherein the fluid circuit comprises at least a portion of a hemofiltration system.

17. The fluid processing apparatus of claim 14, wherein the fluid circuit comprises at least a portion of a hemodialysis system.

18. The fluid processing apparatus of claim 14, wherein the connector is releasably coupled to the fluid container.

19. The fluid processing apparatus of claim 14, wherein the connector has a tip end tapered to form a spike, and the connector first inlet and the connector second outlet are disposed proximal the tip end.

* * * * *